United States Patent [19]
Ascione et al.

[11] Patent Number: 5,830,437
[45] Date of Patent: Nov. 3, 1998

[54] ORAL HYGIENE METHOD AND COMPOSITION

[75] Inventors: Jean Marc Ascione, Paris; Serge Forestier, Claye-Souilly, both of France

[73] Assignee: L'Oreal, Paris, France

[21] Appl. No.: 256,609

[22] PCT Filed: Jan. 13, 1993

[86] PCT No.: PCT/FR93/00028

§ 371 Date: Sep. 14, 1994

§ 102(e) Date: Sep. 14, 1994

[87] PCT Pub. No.: WO93/13747

PCT Pub. Date: Jul. 22, 1993

[30] Foreign Application Priority Data

Jan. 15, 1992 [FR] France ................................. 92 00352

[51] Int. Cl.$^6$ ....................................................... A61K 7/16
[52] U.S. Cl. ................................................. 424/49; 424/55
[58] Field of Search ........................................ 424/49, 55

[56] References Cited

U.S. PATENT DOCUMENTS

| | | | |
|---|---|---|---|
| 4,992,258 | 2/1991 | Mason | 424/49 |
| 5,093,170 | 3/1992 | Degenhardt et al. | 424/55 X |
| 5,120,460 | 6/1992 | Asai et al. | 424/55 X |
| 5,292,501 | 3/1994 | Degenhardt et al. | 424/55 X |

*Primary Examiner*—Paul F. Shaver
*Attorney, Agent, or Firm*—Jacobson, Price, Holman & Stern, PLLC

[57] ABSTRACT

Oral hygiene composition characterized by having at least one hydrocarbonated polymer with a linear or cross-linked structure, chiefly consisting of units of formula (Ia) or (I), in which R denotes H or $CH_2OH$, A denotes an alkaline metal or an ammonium, amine or alkanolamine salt, the average frequency of units corresponding to a carboxylate/hydroxymethyl ratio greater than 0.5 in the polymer. The invention also concerns a physiologically acceptable carrier. The use of the composition in oral hygiene and processes putting it into effect are also disclosed.

13 Claims, No Drawings

ORAL HYGIENE METHOD AND COMPOSITION

The present invention concerns compositions for oral use for avoiding stain formation on teeth and adhesion of exogenous substances. The invention also relates to an oral hygiene method using such compositions.

The formation of stains on teeth poses an aesthetic problem for many individuals, in particular those susceptible to staining from tar and tartar or to stains caused by ingested food, smokers and tea or coffee drinkers.

Adsorption and retention of food substances contributes greatly to stain formation on both natural and artificial teeth, partly caused by the adhesion of exogenous substances. Tea, coffee, wine, red fruits and tobacco are the main causes of stain formation.

Antibacterial antiplaque agents can also cause stain formation: biguanidohexanes such as chlorhexidine and alexidine and quaternary ammonium salts such as benzethonium chloride and cetylpyridinium chloride can cause stains to form.

Patents U.S. Pat. No. 4,224,309, U.S. Pat. No. 4,118,474 and U.S. Pat. No. 4,118,473 describe the use of additives such as 2-phosphonobutane-1,2,4-tricarboxylic acid, phosphono- acetic acid and iminodiacetic N-methylenephosphonic acid to reduce stain formation on teeth which is caused by continual use of antibacterial agents.

Document EP-A-373 688 describes the use of organopolysiloxanes to prevent tar, stains, tartar and food particles from adhering to the teeth.

Finally, some synthetic linear anionic polymers, polycarboxylates, have been described for oral application, particularly in association with a source of fluoride ions to encourage the action of some antitartar agents based on alkaline polyphosphates by impeding their enzymatic hydrolysis by saliva. Examples of these polymers include crosslinked carboxyvinyl compounds, sold by BF GOODRICH under the trade name "CARBOPOL" (CARBOPOL 934, CARBOPOL 940, CARBOPOL 941), copolymers of maleic anhydride and methylvinylether with an average molecular weight of 30 000 to 1 000 000, preferably 30 000 to 500 000, sold by GAF CORPORATION under the trade name "GANTREZ", in particular "GANTREZ S-97 PHARMACEUTICAL GRADE" (average molecular weight 70 000), and copolymers of vinyl acetate and crotonic acid, such as those sold by HOECHST under the trade name "ARISTOFLEX A".

We have now developed, surprisingly, linear or crosslinked synthetic hydrocarbon polymers which contain carboxylate and hydroxymethyl groups which effectively prevent stain formation on teeth. The anti-staining action has been demonstrated in vitro by colorimetric measurement of hydroxyapatite (HAP) powder pellets treated with a solution of the polymer compared with untreated pellets of HAP powder. In addition, compositions for oral use containing these polymers not only prevent stain formation as described above, i.e. due to retention and/or adsorption of food substances, but also prevent darkening of natural or artificial teeth caused by the presence of known antibacterial antiplaque agents. The compositions also readily prevent adhesion of exogenous substances to the teeth and are active in preventing the appearance of dental plaque and tartar. They also contribute generally to oral hygiene.

The present invention thus concerns a composition for oral use, characterized in that it comprises at least one linear or crosslinked hydrocarbon polymer which is principally constituted by units with the following formula:

or

where:
R represents H or $CH_2OH$,
A represents an alkali metal or an ammonium, amine or alkanolamine salt, the average frequency of the units corresponding to a carboxylate/hydroxymethyl ratio greater than 0.5 in the polymer, and
a physiologically acceptable vehicle.

The units with formula (Ia) and (Ib) can be disposed in any order and the average frequency of the units in the polymer preferably corresponds to a carboxylate/hydroxymethyl ratio of between 1.1 and 16, better still between 2 and 9. The average degree of polymerization is 3 to 1 000, preferably 50 to 600.

"Oral use" means the products are not ingested, but can be retained in the mouth for a sufficient period to allow contact with the entire dental surface.

The polymers used in the oral composition of the invention are particularly described in patent FR-A-2 334 695. They are generally in powder form and are linear or crosslinked polymers which principally contain units with formula (I) above where A represents an alkaline metal such as sodium, or an ammonium, amine or alkanolamine salt.

Preferred examples of these polymers are those in which the carboxylate is a sodium carboxylate. Polymers which are known under the trade names "HYDAGEN F" or "HYDAGEN FN" can be used, for example.

The oral composition of the invention preferably contains an effective quantity of polymers which are marketed under the trade name "HYDAGEN FN". This is a sodium acrylate/vinylcarbinol copolymer.

Oral compositions of the invention containing at least one polymer constituted by units with formulae (Ia) and (Ib) can exist in a number of forms, in particular as sprays, foams, mouthwashes, gargles, powders, dental tablets or granules, chewing gum, dental gel, or toothpastes or gels. The vehicle used depends on the required form.

As well as the polymer(s) constituted by units with formulae (Ia) and (Ib), the oral compositions of the invention can also contain ingredients which are normally used in products for oral use in the appropriate form, either as a vehicle or an active ingredient.

These compositions are prepared using known methods depending on the vehicle selected. The physiologically acceptable medium can differ depending on the selected form of the composition: aqueous solution, hydroalcoholic solution, optionally thickened, gum, paste or solid excipient, etc.

The polymers defined above are present alone or as a mixture in these compositions in effective quantities, i.e. at concentrations of between 0.05% and 10% by weight, preferably between 0.1% and 5% by weight, with respect to the total composition weight.

Depending on the desired form, they can in particular contain at least one polishing agent in proportions of up to 95%. The polishing agents are abrasives which may be mineral or organic in origin. Their nature can differ depending on the vehicle used for the form selected (see below).

In some forms the compositions can contain one or more surfactant(s) which are sufficiently stable and are foaming agents. Suitable surfactants include anionic, amphoteric, zwitterionic, cationic and non-ionic surfactants. Anionic or non-ionic surfactants are preferable.

In general, the surfactants can be present in proportions of up to 20% by weight with respect to the composition, in particular within a range of 0.5% to 5%.

The compositions of the invention can also contain other active oral hygiene ingredients, in particular known active ingredients which can counteract halitosis, such as cyclodextrines or mineral or organic zinc salts, for example zinc halides, zinc acetate, zinc citrate or zinc fluoride.

The compositions can additionally contain other agents which are normally contained in oral compositions, such as cohesive agents, thickening agents, antibiotic agents, sweeteners, moistening agents, cooling agents, preservatives, sugars, dyes, flavorings, aromatizing or palatabilizing agents, peptizing agents, plasticizers, antibacterial or bactericidal agents, vitamins, anticaries agents, antitartar agents, healing agents, vasomotors, clotting agents, active agents for gums and polishing agents. The various agents are present in the composition of the invention, in particular depending on the form it takes.

Thus when the oral composition is a spray, the vehicle can be a hydroalcohol solution and the composition can also contain flavorings, peptizing agents, sweeteners, moistening agents or cooling agents.

When the composition is in the form of a mouthwash, for example, the vehicle can essentially be constituted by an aqueous solution of a foaming surfactant which may optionally contain a thickening agent, and can also contain bactericidal, sweetening and flavoring agents.

When the compositions are in the form of a gargle, they can contain an antibiotic agent as an active ingredient.

When the composition is in the form of a dental gel, for example, it can also contain active ingredients for the gums.

When the composition is in the form of a powder, tablets or granules, it generally contains primarily a foaming surfactant and a polishing agent which is present in proportions of up to 90% to 95% by weight.

When the compositions are in the form of chewing gum, they contain at least one natural or synthetic chewable gum and can contain plasticizers, vitamins, aromatizing or palatabilizing agents, sugars, moistening agents, bactericidal agents, preservatives, dyes and optionally polishing agents.

Examples of gums with sufficient elasticity to be chewed either on their own or as a mixture are natural gums such as Hevea latex, chicle gum, schulong gum and synthetic gums such as polyvinyl acetate and the following synthetic elastomers: silicone rubber and butyl rubber. In general, the gums contain 0.5% to 70% by weight of chewable gum.

Polishing agents can optionally be used in the invention. For the chewing gums, mineral or organic polishing agents which are normally used in chewing gums can be used. Examples are calcium, magnesium and sodium carbonate, calcium phosphates and sulphates, alumina and hydrated alumina, silicas, magnesium oxides, hydroxides, trisilicates and pyrophosphates, and cellulose compounds produced by milling cereals.

When the compositions are in the form of a toothpaste, they can contain a polishing agent in a proportion of up to approximately 6% to 70%, preferably 15% to 25%. This is normally an abrasive mineral polishing agent constituted by one or more compounds which are largely insoluble in water. Examples are sodium or potassium metaphosphates, dihydrated calcium phosphate, dicalcium phosphate, tricalcium phosphate, calcium pyrophosphate, alumina, hydrated aluminas, especially trihydrated aluminas, silicas, aluminium or zirconium silicates, bentonite, magnesium orthophosphate and trimagnesium phosphate.

When the composition is in the form of a transparent gel, a colloidal silica or alkali metal or alkaline-earth (preferably sodium or calcium) aluminosilicate based polishing agent can be used.

In some forms, particularly toothpastes, the composition of the invention can contain one or more cohesive agents. These can be incorporated in proportions of up to 10% by weight with respect to the total composition weight, preferably 0.5% to 3% by weight. They may be selected from natural thickeners such as alginates and pectins, natural gums such as gum tragacanth, xanthane gums, guar gums, carob gums or carragheen gums, or synthetic thickeners, normally derived from cellulose, such as the sodium salt of carboxymethylcellulose, methylcellulose or hydroxyalkylcelluloses or crosslinked polyacrylic acids such as the "CARBOPOLS".

Oral compositions of the invention can also contain a sweetener. Examples of sweeteners are saccharose, lactose, fructose, xylitol, sodium cyclamate, maltose, sodium saccharinate, α-glucosyl/steviolglucoside mixtures, D-mannitol, aspartame, acesulfam K and mixtures thereof.

The sweeteners are present in concentrations of up to 2%.

Moistening agents include sorbitol, glycerol and xylitol used in concentrations of up to 50%.

Cooling agents such as menthol or ethylmaltol can also be added.

Preservatives can be used in the compositions of the invention to ensure high bacteriological purity in the formulations. Examples are methyl parahydroxybenzoate, propyl parahydroxybenzoate, and other known preservatives. They can be present in concentrations of up to 0.5% by weight.

Examples of aromatizing substances for use in compositions of the invention are essences of mint, aniseed, eucalyptus, cinnamon, cloves, sage or liquorice, or of fruits such as lemon, orange, mandarin or strawberry; methyl salicylate can also be used as an aromatizing substance. Aromatizing agents, if used, are present in concentrations of up to 5% by weight of the composition.

When an antibacterial agent is used, as is normal in this type of oral composition, active ingredients are preferably selected of which some are essential oils or substances such as chlorhexidine, alexidine, octinidine, hexetidine, phenoxyethanol, phenethyl alcohol and triclosan.

When present in the composition, the bacterial agents can represent up to 10% by weight of the composition and are preferably present in concentrations of between 0.05% and 2% by weight.

Anticaries agents can be incorporated into oral compositions of the invention, for example sodium monofluorophosphate, sodium or tin fluorides, fluorinated amines and cationic fluoride polymers such as those described in patent FR-A-2 647 012.

Finally, the composition can contain active agents such as antitartar agents, healing agents, vasomotors or clotting agents.

The invention thus concerns the use of a composition comprising a polymer as defined above and a vehicle which is physiologically acceptable for oral hygiene use, in particular for preventing the formation of stains on the teeth, adhesion of exogenous substances to the teeth and dental plaque.

The invention also concerns an oral hygiene method, characterized in that a composition containing at least one linear or crosslinked hydrocarbon polymer is applied in the mouth, the composition being principally constituted by units with the following formula:

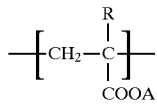

(Ia)

or

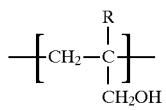

(Ib)

where:

R represents H or $CH_2OH$,

A represents an alkaline metal or an ammonium, amine or alkanolamine salt, the average frequency of the units corresponding to a carboxylate/hydroxymethyl ratio greater than 0.5 in the polymer, and a physiologically acceptable vehicle.

The invention further concerns a method of protecting natural or artificial teeth by preventing the formation of stains on the teeth, by protecting the teeth against adhesion of exogenous substances and against the formation of dental plaque, the method comprising applying the composition of the invention in the mouth.

Application can be effected by gargling, using a mouthwash, dispersing, spraying, chewing, brushing or application with a finger or pad to the teeth and/or gums.

The following examples illustrate the invention but do not limit its scope.

EXAMPLE 1

A toothpaste with the following composition was prepared:

| | |
|---|---|
| Amorphous precipitated silica, sold by RHONE-POULENC under the trade name TIXOSIL 73 | 13 g |
| Amorphous precipitated silica, sold by RHONE-POULENC under the trade name TIXOSIL 43 | 7 g |
| Titanium dioxide | 0.5 g |
| Sodium carboxymethylcellulose, sold by HERCULES under the trade name BLANOSE 9M 31 S | 1.4 g |
| Sorbitol, 70% AM aqueous solution | 22.4 g AM |
| Powdered sodium laurylsulphate, 93% AM, sold by MARCHON under the trade name EMPICOL LZV/E | 1.63 g AM |
| Sodium fluoride | 0.11 g |
| Sodium monofluorophosphate | 0.38 g |
| Sodium acrylate/vinylcarbinol copolymer with MW 7 000-11 000, sold by HENKEL under the trade name HYDAGEN FN | 4 g |
| Sweetener: aspartame | 0.2 g |
| Preservative | qs |
| Flavoring | qs |
| Water qsp | 100 g |

EXAMPLE 2

A toothpaste with the following composition was prepared:

| | |
|---|---|
| Hydrated alumina sold by SOCHALU under the trade name ALUMINE SH 100 | 45 g |
| Titanium dioxide | 1 g |
| Xanthane gum sold by RHONE POULENC under the trade name RHODOPOL 23 SC | 1.2 g |
| Sorbitol, 70% AM aqueous solution | 7 g AM |
| Glycerine | 10 g |
| Powdered sodium laurylsulphate, 93% AM, sold by MARCHON under the trade name EMPICOL LZV/E | 1.86 g AM |
| Sodium fluoride | 0.22 g |
| Sodium saccharinate | 0.2 g |
| Sodium acrylate/vinylcarbinol copolymer with MW 7 000-11 000, sold by HENKEL under the trade name HYDAGEN FN | 1.25 g |
| Flavoring, preservative | qs |
| Water qsp | 100 g |

EXAMPLE 3

A clear tooth gel with the following composition was prepared:

| | |
|---|---|
| Precipitated silica sold by DEGUSSA under the trade name SIDENT 22 S | 8 g |
| Precipitated silica sold by DEGUSSA under the trade name SIDENT 9 | 12 g |
| Sodium carboxymethylcellulose sold by HERCULES under the trade name BLANOSE 12M 31 XP | 0.8 g |
| Sorbitol, 70% AM aqueous solution | 44.8 g AM |
| Powdered sodium laurylsulphate, 93% AM, sold by MARCHON under the trade name EMPICOL LZV/E | 1.4 g AM |
| Sodium saccharinate | 0.15 g |
| Sodium acrylate/vinylcarbinol copolymer with MW 7 000-11 000, sold by HENKEL under the trade name HYDAGEN FN | 0.4 g |
| Polyethylene glycol containing 8 moles ethylene oxide | 2 g |
| Flavoring, preservative, dye | qs |
| Water qsp | 100 g |

EXAMPLE 4

An oral spray with the following composition was prepared:

| | |
|---|---|
| Ethyl alcohol | 42 g |
| Glycerine | 8 g |
| Sodium saccharinate | 0.05 g |
| Sodium acrylate/vinylcarbinol copolymer with MW 7 000-11 000, sold by HENKEL under the trade name HYDAGEN FN | 0.25 g |
| Flavoring | 1 g |
| Peptizer | 2 g |
| Water qsp | 100 g |

EXAMPLE 5

A mouthwash with the following composition was prepared:

| | |
|---|---|
| Sodium saccharinate | 0.02 g |
| Trisodium phosphate | 0.04 g |
| Monosodium phosphate | 0.08 g |
| Ethyl alcohol | 5 g |
| Sodium acrylate/vinylcarbinol copolymer with MW 7 000-11 000, sold by HENKEL under the trade name HYDAGEN FN | 0.5 g |
| Sorbitol, 70% AM in aqueous solution | 3.5 g AM |
| Flavoring | 0.15 g |
| Peptizer | 1.5 g |

EXAMPLE 6

A dental gel with the following composition was prepared:

| | |
|---|---|
| Crosslinked polyacrylic acid, neutralized with NaOH, sold by GOODRICH under the trade name CARBOPOL 940 before neutralization | 0.5 g |
| Sodium acrylate/vinylcarbinol copolymer with Mw 7 000-11 000, sold by HENKEL under the trade name HYDAGEN FN | 0.1 g |
| Sorbitol, 70% AM in aqueous solution | 7 g AM |
| Sodium saccharinate | 0.02 g |
| Glycerine | 20 g |
| Peptizer | 2 g |
| Flavoring | 0.1 g |
| Preservative | qs |
| Water qsp | 100 g |

EXAMPLE 7

A chewing gum with the following composition was prepared:

| | |
|---|---|
| Elastic base | 25 g |
| Sorbitol, 70% AM in aqueous solution | 10.5 g AM |
| Powdered sorbitol | 53.4 g |
| Sodium acrylate/vinylcarbinol copolymer with MW 7 000-11 000, sold by HENKEL under the trade name HYDAGEN FN | 0.1 g |
| Glycerine | 5 g |
| Flavoring | 1.5 g |

EXAMPLE 8

A toothpaste with the following composition was prepared:

| | |
|---|---|
| Amorphous precipitated silica, sold by RHONE-POULENC under the trade name TIXOSIL 73 | 12 g |
| Amorphous precipitated silica, sold by RHONE-POULENC under the trade name TIXOSIL 333 | 8 g |
| Powdered sodium laurylsulphate, 93% AM, sold by MARCHON under the trade name EMPICOL LZV/E | 1.8 g AM |
| Xanthane gum sold by RHONE POULENC under the trade name RHODOPOL 23SC | 1.2 g |
| Titanium dioxide | 0.6 g |
| Sorbitol, 70% AM aqueous solution | 30 g AM |
| Methyl parahydroxybenzoate | 0.2 g |
| Flavoring | qs |
| Polyethylene glycol containing 8 moles ethylene oxide | 1 g |
| Sodium acrylate/vinylcarbinol copolymer with MW 22500 and a degree of polymerization between 200 and 220 | 0.5 g |
| Sodium saccharinate | 0.2 g |
| Water qsp | 100 g |

We claim:

1. Composition for oral use comprising at least one linear or crosslinked hydrocarbon polymer which is principally constituted by units with the following formula:

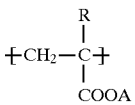

or

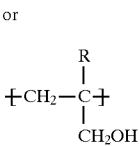

where:

R represents H or $CH_2OH$,

A represents an alkaline metal or an ammonium, amine or alkanolamine salt, the average frequency of the units corresponding to a carboxylate/hydroxymethyl ratio greater than 0.5 in the polymer, and a physiologically acceptable vehicle.

2. Composition according to claim 1 wherein the average degree of polymerization of said polymer is between 3 and 1 000.

3. Composition according to claim 1 wherein the average frequency of the units in the polymer corresponds to a carboxylate/hydroxymethyl ratio of between 1.1 and 16.

4. Composition according to claim 1 wherein A represents Na in formula (Ia).

5. Composition according to claim 1 which contains 0.05% to 10% by weight of polymer with respect to the total composition weight.

6. Composition according to claim 1 which contains 0.1% to 5% by weight of polymer with respect to the total composition weight.

7. Composition according to claim 1 which is in the form of a gel or toothpaste, mouthwash, foam, gargle, powder, dental tablet or granules, dental spray, dental gel or chewing gum.

8. Composition according to claim 1 which further contains a polishing agent which is present in proportions of up to 95% by weight with respect to the total composition weight.

9. Composition according to claim 1 which contains up to 20% by weight with respect to the total composition weight of anionic, non-ionic, zwitterionic, amphoteric or cationic surfactants.

10. Composition according to claim 1 which contains at least one cohesive agent, thickener, sweetener, moistening agent, cooling agent, plasticizer, flavoring agent, aromatizing or peptizing agent or sweetener substance, palatabilizing agent, preservative, antibacterial agent, antibiotic agent, anticaries agent, vitamin, antitartar agent, dye, healing agent, vasomotor, clotting agent, active ingredient for gums, or active ingredient for inhibiting halitosis.

11. Oral hygiene method comprising applying a composition for oral use in the mouth, the composition comprising a linear or crosslinked hydrocarbon polymer which is principally constituted by units with the following formula:

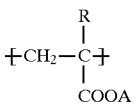

or

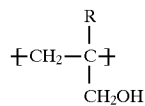

where:

R represents H or CH₂OH,

A represents an alkaline metal or an ammonium, amine or alkanolamine salt, the average frequency of the units corresponding to a carboxylate/hydroxymethyl ratio greater than 0.5 in the polymer, and a physiologically acceptable vehicle.

12. Method of protecting natural or artificial teeth against stains, adhesion of exogenous substances and dental plaque comprising applying an effective quantity of a composition to the teeth and/or the gums, the composition comprising at least one linear or crosslinked hydrocarbon polymer which is principally constituted by units with the following formula:

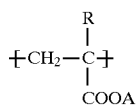

or

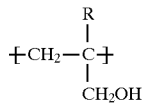

where:

R represents H or CH₂OH,

A represents an alkaline metal or an ammonium, amine or alkanolamine salt, the average frequency of the units corresponding to a carboxylate/hydroxymethyl ratio greater than 0.5 in the polymer, and a physiologically acceptable vehicle.

13. Composition according to claim 1 wherein the averge degree of polymerization of said polymer is between 50 to 600.

* * * * *